United States Patent [19]

Buzzetti et al.

[11] Patent Number: 5,122,537
[45] Date of Patent: Jun. 16, 1992

[54] ARYLVINYLAMIDE DERIVATIVES AND PHARMACEUTICAL USE

[75] Inventors: Franco Buzzetti, Monza; Angelo Crugnola, Varese, both of Italy

[73] Assignee: Farmitalia Carlo Erba S.r.l., Milan, Italy

[21] Appl. No.: 608,409

[22] Filed: Nov. 2, 1990

[30] Foreign Application Priority Data

Jan. 16, 1990 [GB] United Kingdom ............... 9000950

[51] Int. Cl.$^5$ ............... A61K 31/165; C07C 233/22
[52] U.S. Cl. ............... 514/510; 514/307;
514/309; 514/311; 514/312; 514/415; 514/418;
514/419; 514/522; 514/630; 546/141; 546/142;
546/146; 546/147; 546/153; 546/155; 546/175;
548/484; 548/485; 548/486; 548/496; 548/503;
558/414; 560/139; 564/219
[58] Field of Search ............... 564/219; 514/630, 510,
514/522; 558/414; 560/139

[56] References Cited

U.S. PATENT DOCUMENTS 3,056,790 10/1962 Cannon ........................... 260/287
4,686,308 8/1987 Umezawa et al. ............... 564/219
4,925,877 5/1990 Umezawa et al. ............... 564/219 X

FOREIGN PATENT DOCUMENTS 1902402 11/1969 Fed. Rep. of Germany .
89/04659 6/1989 PCT Int'l Appl. .

OTHER PUBLICATIONS

Redeker et al., Überführung von N-Acylaminosäuren in Enamine durch Beckman Fragmentierung von alpha-Acylaminoketoximen, Tetrahedron Letters, vol. 22, No. 43, pp. 4263-4264, 1981, Great Britain.
N. S. Narasimhan et al., "Synthetic Application of Lithiation Reactions VII-Tetrahedron", vol. 31, pp. 1005 to 1009, 1975, Great Britain.
Shaw et al, "Stereochemistry of the β-Phenylserines: Improved Preparation of Allophenylserine", J. Am. Chem. Soc. 75, pp. 3421-3424, 1953, Ames, Iowa.
McOmie et al, "Demethylation of Aryl Methyl Ethers by Boron Tribromide", Tetrahedron, vol. 74, pp. 7789-7797, 1968, Great Britain.
Johnson et al., "The Sterochemistry of Oxidation at Sulfur. Oxidation of 4-Substituted Thianes to Sulfoxides", J. Am. Chem. Soc. 87, pp. 1103-1119, 1965.
Norman G. Gaylord, "Reduction with Complex Metal Hydrides", pp. 762-837, 1956, New York, New York.
H. Gilman et al., "Organic Syntheses-Nitrostyrene", Colective vol. 1, pp. 413-415, London, 1941.
Ferguson et al., "Isolation and Analysis of an Abelson Murine Leukemia Virsu-encoded Tyrosine-specific Kinase Produced in Escherichia coli", J. Biol. Chem., vol. 6, pp. 3652-3657, 1985, U.S.A.
Trost et al., "New Synthetic Methods Secoalkylative Approach to Grandisol", J. Org. Chem., vol. 40, No. 13, p. 2013, 1975.

Abstract of EP 213,320, Pharmaceuticals, week 8710, p. 3 (1987).

(List continued on next page.)

Primary Examiner—Richard L. Raymond
Attorney, Agent, or Firm—Nikaido, Marmelstein Murray & Oram

[57] ABSTRACT

The invention relates to new arylvinylamide derivatives of formula

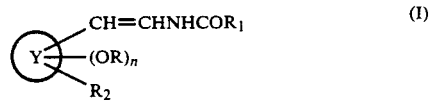

(I)

wherein
Y is a bicyclic ring system chosen from (A), (B), (C), (D), and (E);

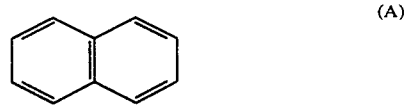

(A)

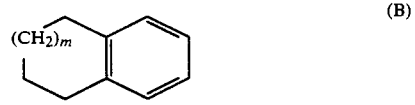

(B)

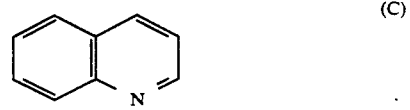

(C)

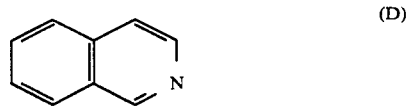

(D)

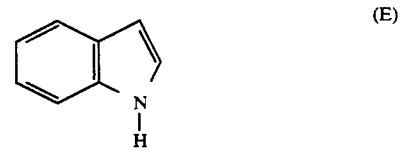

(E)

in which m is zero, 1 or 2;
R is hydrogen, a $C_1$–$C_6$ alkyl or $C_1$–$C_6$ alkanoyl group;
$R_1$ is hydrogen or $C_1$–$C_6$ alkyl;
$R_2$ is hydrogen, halogen, cyano or $C_1$–$C_6$ alkyl; and
n is an integer of 1 to 3; and wherein each of the substituents —CH=CHNHCOR$_1$, OR and R$_2$ may be independently on either of the aryl and heteroaryl moieties of the bicyclic ring system (A), (C), (D) and (E); whereas only the benzene ring may be substituted in the bicyclic ring system (B), which are useful as tyrosine kinase inhibitors.

6 Claims, No Drawings

OTHER PUBLICATIONS

Abstract of EP 238,868, Pharmaceuticals, week 8739, p. 5 (1987).

Anderson et al., "Synthesis of Erbstatin, a Naturally Occurring Inhibitor of Tyrosine-Specific Protein Kinase", *J. Org. Chem.* (1987) 52:2945–2947.

Hangauer, "Total Synthesis of Erbstatin", *Tetrahedron Letters*, 27:5799–5802 (1986).

Dow et al., "Total Synthesis of Erbstatin", *Tetrahedron Letters*, 28:2217–2220 (1987).

Mulzer et al., "Decarboxylative Dehydration of β-Hydroxycarboxylic Acids by Redox Condensation: A Novel Olefin Synthesis", Angew. Chem. Int. Ed. 16, pp. 255 and 256 (1977).

Hara et al., "A New Synthesis of Olefins from β-Hydroxy Carboxylic Acids", *Tetrahedron Letters*, 19:1545–1548, (1975).

ARYLVINYLAMIDE DERIVATIVES AND PHARMACEUTICAL USE

The present invention relates to new arylvinylamide derivatives, to a process for their preparation, to pharmaceutical compositions containing them and to their use as therapeutic agents. The present invention provides novel compounds having the general formula (I)

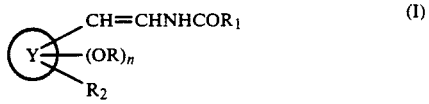

wherein
Y is a bicyclic ring system chosen from (A), (B), (C), (D), and (E):

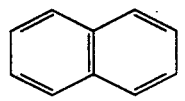

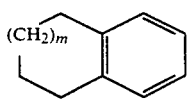

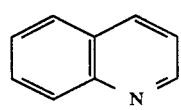

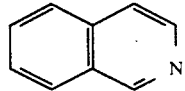

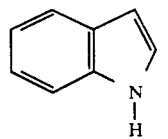

in which m is zero, 1 or 2;
R is hydrogen, a $C_1-C_6$ alkyl or $C_1-C_6$ alkanoyl group;
$R_1$ is hydrogen or $C_1-C_6$ alkyl;
$R_2$ is hydrogen, halogen, cyano or $C_1-C_6$ alkyl; and
m is an integer of 1 to 3; and wherein each of the substituents —CH=CHNHCOR$_1$, OR and R$_2$ may be independently on either of the aryl and heteroaryl moieties of the bicyclic ring system (A), (C), (D) and (E); whereas only the benzene ring may be substituted in the bicyclic ring system (B).

When n is 2 or 3, the —OR groups may be the same or different.

The invention includes within its scope all the possible isomers, stereoisomers, in particular Z and E isomers and their mixtures, and the metabolites and the metabolic precursors or bio-precursors (otherwise known as pro-drugs) of the compounds of formula (I). Namely the invention includes compounds which have a different formula to formula (1) above but which nevertheless upon administration to a human being are converted directly or indirectly in vivo into a compound of formula (I).

A halogen atom may be a fluorine, chlorine, bromine or iodine atom.

The alkyl groups, and the alkyl moiety in the alkanoyl groups, may be a branched or straight alkyl chain. A $C_1-C_6$ alkyl group is preferably a $C_1-C_4$ alkyl group, e.g. methyl, ethyl, propyl, isopropyl, butyl, sec. butyl or tert. butyl, in particular methyl or ethyl. A $C_1-C_6$ alkanoyl group is preferably a $C_1-C_4$ alkanoyl group in particular acetyl, propionyl or butyryl.

Preferred compounds according to the present invention are the compounds of formula (I), wherein
Y is a bicyclic ring system as defined above;
R is hydrogen or $C_1-C_4$ alkyl;
$R_1$ is hydrogen or $C_1-C_4$ alkyl;
$R_2$ is hydrogen; and
n is as defined above.

More preferred compounds of the invention are those of formula (I),
wherein
Y is a bicyclic ring system as defined above; each of R, $R_1$ and $R_2$ is hydrogen; and
n is 1 or 2.

For ring systems (A) and (B), preferably the group —CH=CH NHCOR$_1$ is in the 1- or 2-position, R$_2$ is hydrogen and there is a group OR, typically a hydroxy group, in the 1-, 2-, 3- or 4-position or there are groups OR', typically hydroxy groups, in the 1, 4- ; 1, 3-; 3, 4-; 2, 3- or 2, 4-positions. Of course the —CH=CH NHCOR$_1$ group and a OR group do not occupy the same position. This applies to the preferred configurations of substituents on ring systems (C), (D) and (E) mentioned below.

For ring system (C), the group —CH=CH NHCOR$_1$ may be in the 2-, 3-, 4-, 5- or 8-position. Preferably R$_2$ is hydrogen and n is 0 or 1. When n is 1, there can be a OR group, typically a hydroxy group, in the 2-, 3-, 4-, 5-, 6-, 7- or 8-position. The group —CH=CH NHCOR$_1$ is preferably in the 1- or 3-position for ring system (D), in which case also R$_2$ preferably is hydrogen and a OR group, typically a hydroxy group, is present in the 1-, 3-, 4-, 5-, 6-, 7- or 8-position.

The group —CH=CH NHCOR$_1$ may be in the 2-, 3-, 4-, 5-, 6- or 7-position for ring system (E). Preferably R$_2$ is hydrogen and n is 1. A OR group, generally a hydroxy group, can be present in the 2-, 3-, 4-, 5-, 6- or 7-position.

Examples of specific compounds of the invention are the following compounds which, when appropriate may be either Z- or E-diastereoisomers or Z,E-mixtures of said diastereomers:

2-(N-formylaminovinyl)-1-hydroxynaphthalene;
2-(N-formylaminovinyl)-3-hydroxynaphthalene;
2-(N-formylaminovinyl)-4-hydroxynaphthalene;
2-(N-formylaminovinyl)-1,4-dihydroxynaphthalene;
2-(N-formylaminovinyl)-1,3-dihydroxynaphthalene:
1-(N-formylaminovinyl)-2-hydroxynaphthalene;
1-(N-formylaminovinyl)-3-hydroxynaphthalene;
1-(N-formylaminovinyl)-4-hydroxynaphthalene;
1-(N-formylaminovinyl)-3,4-dihydroxynaphthalene;
1-(N-formylaminovinyl)-2,4-dihydroxynaphthalene;
1-(N-formylaminovinyl)-2,3-dihydroxynaphthalene;
1-(N-formylaminovinyl)-2-hydroxytetrahydronaphthalene;
1-(N-formylaminovinyl)-3-hydroxy-tetrahydronaphthalene;

1-(N-formylaminovinyl)-4-hydroxytetrahydronaphthalene;
1-(N-formylaminovinyl)-3,4-dihydroxy-tetrahydronaphthalene;
1-(N-formylaminovinyl)-2,4-dihyroxytetrahydronaphthalene;
1-(N-formylaminovinyl)-2,3-dihyroxytetrahydronaphthalene;
2-(N-formylaminovinyl)-1-hydroxy-tetrahydronaphthalene;
2-(N-formylaminovinyl)-3-hydroxy-tetrahydronaphthalene;
2-(N-formylaminovinyl)-4-hydroxy-tetrahydronaphthalene;
2-(N-formylaminovinyl)-1,3-dihydroxytetrahydronaphthalene;
2-(N-formylaminovinyl)-1,4-dihydroxy-tetrahydronaphthalene;
2-(N-formylaminovinyl)-3,4-dihydroxy-tetrahydronaphthalene;
2-(N-formylaminovinyl)quinoline;
2-(N-formylaminovinyl)-3-hydroxyquinoline;
2-(N-formylaminovinyl)-4-hydroxyquinoline;
2-(N-formylaminovinyl)-5-hydroxyquinoline;
2-(N-formylaminovinyl)-6-hydroxyquinoline;
2-(N-formylaminovinyl)-7-hydroxyquinoline;
2-(N-formylaminovinyl)-8-hydroxyquinoline;
3-(N-formylaminovinyl)-quinoline
3-(N-formylaminovinyl)-2-hydroxyquinoline;
3-(N-formylaminovinyl)-4-hydroxyquinoline;
3-(N-formylaminovinyl)-5-hydroxyquinoline;
3-(N-formylaminovinyl)-6-hydroxyquinoline;
3-(N-formylaminovinyl)-7-hydroxyquinoline;
3-(N-formylaminovinyl)-8-hydroxyquinoline;
4-(N-formylaminovinyl)-quinoline;
4-(N-formylaminovinyl)-2-hydroxyquinoline;
4-(N-formylaminovinyl)-3-hydroxyquinoline;
4-(N-formylaminovinyl)-5-hydroxyquinoline;
4-(N-formylaminovinyl)-6-hydroxyquinoline;
4-(N-formylaminovinyl)-7-hydroxyquinoline;
4-(N-formylaminovinyl)-8-hydroxyquinoline;
5-(N-formylaminovinyl)-quinoline;
5-(N-formylaminovinyl)-2-hydroxyquinoline;
5-(N-formylaminovinyl)-3-hydroxyquinoline;
5-(N-formylaminovinyl)-4-hydroxyquinoline;
5-(N-formylaminovinyl)-6-hydroxyquinoline;
5-(N-formylaminovinyl)-7-hydroxyquinoline;
5-(N-formylaminovinyl)-8-hydroxyquinoline;
8-(N-formylaminovinyl)-2-hydroxyquinoline;
8-(N-formylaminovinyl)-3-hydroxyquinoline;
8-(N-formylaminovinyl)-4-hydroxyquinoline;
8-(N-formylaminovinyl)-5-hydroxyquinoline;
8-(N-formylaminovinyl)-6-hydroxyquinoline;
8-(N-formylaminovinyl)-7-hydroxyquinoline;
1-(N-formylaminovinyl)-3-hydroxyisoquinoline;
1-(N-formylaminovinyl)-4-hydroxyisoquinoline;
1-(N-formylaminovinyl)-5-hydroxyisoquinoline;
1-(N-formylaminovinyl)-6-hydroxyisoquinoline;
1-(N-formylaminovinyl)-7-hydroxyisoquinoline;
1-(N-formylaminovinyl)-8-hydroxyisoquinoline;
3-(N-formylaminovinyl)-1-hydroxyisoquinoline;
3-(N-formylaminovinyl)-4-hydroxyisoquinoline;
3-(N-formylaminovinyl)-5-hydroxyisoquinoline;
3-(N-formylaminovinyl)-6-hydroxyisoquinoline;
3-(N-formylaminovinyl)-7-hydroxyisoquinoline;
3-(N-formylaminovinyl)-8-hydroxyisoquinoline;
2-(N-formylaminovinyl)-3-hydroxyindole;
2-(N-formylaminovinyl)-4-hydroxyindole;
2-(N-formylaminovinyl)-5-hydroxyindole;
2-(N-formylaminovinyl)-6-hydroxyindole;
2-(N-formylaminovinyl)-7-hydroxyindole;
3-(N-formylaminovinyl)-2-hydroxyindole;
3-(N-formylaminovinyl)-4-hydroxyindole;
3-(N-formylaminovinyl)-5-hydroxyindole;
3-(N-formylaminovinyl)-6-hydroxyindole;
3-(N-formylaminovinyl)-7-hydroxyindole;
4-(N-formylaminovinyl)-2-hydroxyindole;
4-(N-formylaminovinyl)-3-hydroxyindole;
4-(N-formylaminovinyl)-5-hydroxyindole;
4-(N-formylaminovinyl)-6-hydroxyindole;
4-(N-formylaminovinyl)-7-hydroxyindole;
5-(N-formylaminovinyl)-2-hydroxyindole;
5-(N-formylaminovinyl)-3-hydroxyindole;
5-(N-formylaminovinyl)-4-hydroxyindole;
5-(N-formylaminovinyl)-6-hydroxyindole;
5-(N-formylaminovinyl)-7-hydroxyindole;
6-(N-formylaminovinyl)-2-hydroxyindole;
6-(N-formylaminovinyl)-3-hydroxyindole;
6-(N-formylaminovinyl)-4-hydroxyindole;
6-(N-formylaminovinyl)-5-hydroxyindole;
6-(N-formylaminovinyl)-7-hydroxyindole;
7-(N-formylaminovinyl)-2-hydroxyindole;
7-(N-formylaminovinyl)-3-hydroxyindole;
7-(N-formylaminovinyl)-4-hydroxyindole;
7-(N-formylaminovinyl)-5-hydroxyindole;
7-(N-formylaminovinyl)-6-hydroxyindole;
1-(N-formylaminovinyl)-2-methoxynaphthalene;
1-(N-formylaminovinyl)-2-methoxy-5,6,7,8-tetrahydronaphthalene; and
1-(N-formylaminovinyl)-2-acetoxynaphthalene.

The compounds of the invention can be obtained by a process comprising:

a) dehydrative decarboxylation of a β-hydroxy-α-acylamino acid of formula (II)

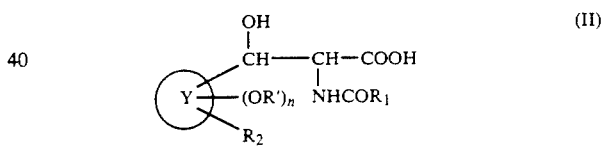

wherein

Y, $R_1$, $R_2$ and n are as defined above and R' is $C_1$–$C_6$ alkyl, so obtaining a compound of formula (I) wherein R is $C_1$–$C_6$ alkyl and Y, n, $R_1$ and $R_2$ are as defined above; and, if desired, the de-etherification of the compound of formula (I) thus obtained in which R is $C_1$–$C_6$ alkyl so as to obtain a corresponding compound of formula (I) wherein R is hydrogen;

and if desired, the acylation of the compound of formula (I) thus obtained in which R is hydrogen so as to obtain a corresponding compound of formula (I) wherein R is a $C_1$–$C_6$ alkanoyl group; or b) thermolytic elimination on a benzylic α-phenylsulfoxido-β-acylamino derivative of formula (III)

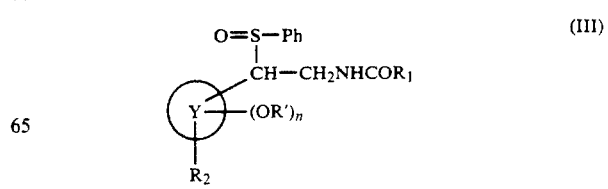

wherein
Ph means phenyl, Y, $R_1$, $R_2$ and n are as defined above and R' is $C_1$-$C_6$ alkyl so obtaining a compound of formula (I) wherein R is $C_1$-$C_6$ alkyl and Y, $R_1$, $R_2$ and n are as defined above and, if desired, the de-etherification of the compound of formula (I) thus obtained in which R is $C_1$-$C_6$ alkyl so as to obtain a corresponding compound of formula (I) wherein R is hydrogen;

and if desired, the acylation of the compound of formula (I) thus obtained in which R is hydrogen so as to obtain a corresponding compound of formula (I) wherein R is a $C_1$-$C_6$ alkanoyl group.

The dehydrative decarboxylation of a compound of formula (II) may be carried out with the aid of a dimethylformamide (DMF) acetal, preferably N,N-dimethylformamide dimethyl acetal as described by Shoji Hara et al. in Tetrahedron Letters 19, 1545 (1975). The reaction may be performed in an inert solvent, e.g. chloroform, methylene chloride or 1,2-dichloroethane, at temperatures ranging from about 0° to about 100° C. With preference the reaction is carried out with an excess of DMF acetal (about 6 moles) in dry chloroform at reflux temperatures.

Alternatively the dehydrative decarboxylation of a compound of formula (II) may be carried out by redox condensation with triphenylphosphine and diethyl azodicarboxylate according to Johann Mulzer et al. (Angew.Chem. Int. Ed. 1977,16,255). The reaction may be performed in an ethereal organic solvent, like diethyl ether or tetrahydrofuran at temperatures ranging from about −10° C. to about 50° C. and for reaction times varying from about 10 min to about 2 hrs. Preferably theredox condensation is performed with equimolar amounts of the reagents in tetrahydrofuran solution at temperatures of about 0°–10° C. for about 10 min.

The thermolysis of a compound of formula (III) may be carried out in a high boiling inert solvent, e.g. chlorobenzene, toluene or xylene in the presence of a basic agent, e.g. sodium carbonate, potassium carbonate or calcium carbonate at temperatures ranging from about 100° to about 200° C. Preferably the thermolytic elimination is performed in refluxing toluene solution in the presence of sodium carbonate.

The de-etherification of a compound of formula (I), wherein R is $C_1$-$C_6$ alkyl, so as to obtain a compound of formula (I) wherein R is hydrogen may be performed by well known methods in organic chemistry.

In the case of a phenolic methyl ether the cleavage can be carried out for example with boron tribromide as described by J. F. W. McOmie in Tetrahedron 24, 2289 (1968). It is advisable to use 1 mol of boron tribromide per ether group together with an extra mol of reagent for each group containing a potentially basic N or O. The reaction may be performed in an inert organic solvent such as methylene chloride, pentane or benzene under a nitrogen atmosphere at temperatures ranging from about −7B° C. to about room temperature.

Acylation of a compound of formula (I), wherein R is hydrogen, so as to obtain a corresponding compound of formula (I), wherein R is a $C_1$-$C_6$ alkanoyl group, may be obtained by reaction with a reactive derivative of a suitable carboxylic acid, such as an anhydride or halide, in the presence of a basic agent, at temperatures ranging from about 0° C. to about 50° C. Preferably the acylation is carried out by reaction with the respective anhydride in the presence of an organic base, such as pyridine. The compounds of formula (II) may be obtained according to known procedures, for example according to the reaction schema A. described herebelow.

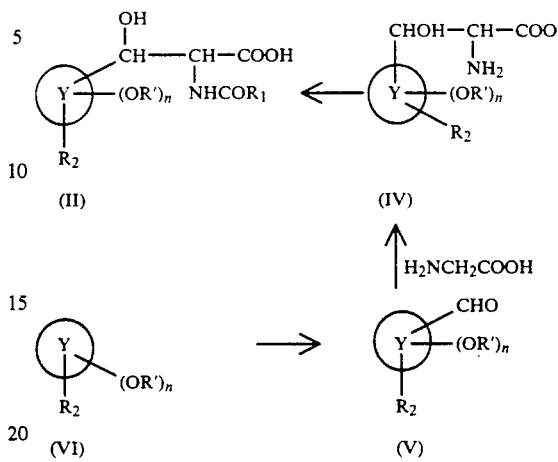

wherein
Y, R', $R_1$, $R_2$ and n are defined above. Accordingly a compound of formula (II) can be obtained by acylating the respective amino compound of formula (IV), wherein, Y, R', $R_2$ and n are as defined above, with a suitable acylating agent using know methods. For example a compound of formula (II) in which $R_1$ is hydrogen can be obtained by reaction with excess of acetic-formic anhydride, at temperatures ranging from about −15 to about 25° C.

A compound of formula (II) in which R is $C_1$-$C_6$ alkyl can be obtained for instance by reaction with a reactive derivative of a suitable aliphatic carboxylic acid, such as an anhydride or halide, in the presence of a basic agent at temperatures ranging from about 0° to about 50° C. Preferably the acylation is carried out by reaction with the respective anhydride in the presence of an organic base, such as pyridine. The acylation of the compound of formula (IV) to form the compound of formula (II) and the dehydrative decarboxylation of the compound of formula (II) can be carried out in discrete sequential steps.

In some cases the dehydrative decarboxylation, described above under process-variant a), can be carried out simultaneously with the acylation of a compound of formula (IV). Thus for example, when a compound of formula (IV) is formylated with a mixture of formic acid and acetic anhydride at room temperature, so as to obtain a compound of formula (II), in which $R_1$ is hydrogen, some of the obtained compounds of formula (II), in particular those wherein Y is naphthyl, are not stable. In fact under these reaction conditions such compounds undergo a dehydrative decarboxylation to provide compounds of formula (I).

The compound of formula (IV) can be obtained by reacting a compound of formula (V), wherein Y, R', $R_2$ and r are as defined above, with glycine. This condensation may be carried out e.g. according to K. N. F. Shaw et al. (J. Am. Chem. Soc. 1953, 75, 3421). The ratio of the reagents is not critical, but in general 2 mol equivalents of the aldehyde component is applied. The condensation may be performed in water or in an aqueous solvent such as aqueous ethanol in the presence of a basic catalyst. Preferably the condensation is carried out in water in the presence of 15 mol equivalent sodium hydroxide. The reaction temperature may very from about 0° C. to about 50° C., with a temperature range from 15 to 25° C. being the preferred. During the condensation a mixture of threo- and erythro-diastereomers are formed, which ratio increases with time. In order to obtain principally the threo form long reaction times, ranging from 20 to 24 hrs, are chosen. After the condensation reaction the N-benzal intermediate formed is hydrolyzed without isolation by treatment with hydrochloric acid at temperatures ranging from about 10 to 30° C.

The compounds of formula (V) may be obtained according to known methods from compounds of formula (VI) wherein Y, R', $R_2$ and n are as defined above. For example the phenolic compound formula (VI) may be treated with chloroform and alkali hydroxides in aqueous or aqueous alcoholic solution according to the well known method of Reimer-Tiemann. If the starting material is an aromatic methylether the method described by N. S. Narasimhan et al. in Tetrahedron 31, 1005 (1975) can be applied.

Accordingly, the methylether of formula (VI) is lithiated with butyl lithium in refluxing ether. Treatment of the organometallic compound with N-methylformanilide furnishes the formuyl derivative.

The compounds of formula (VI) are known or may be obtained by known methods from known compounds.

The compounds of formula (III) may be obtained according to scheme B described herebelow.

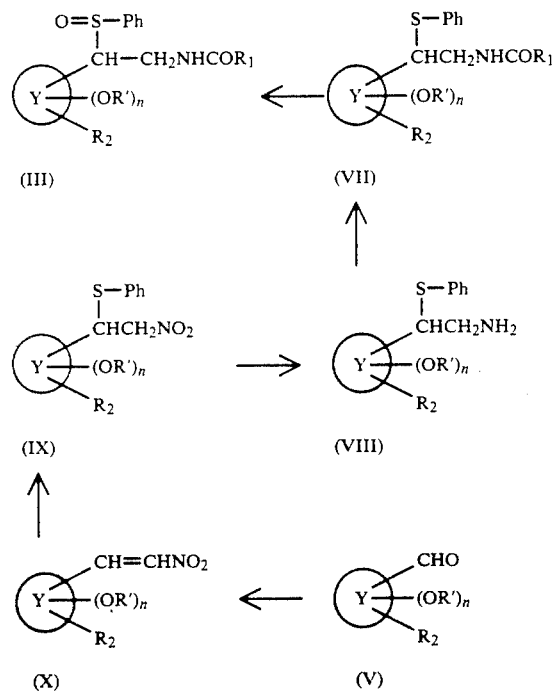

wherein
Y, Ph, R', $R_1$, $R_2$ and n are as defined above.

Accordingly a compound of formula (III) can be obtained from a compound of formula (VII) wherein Y, R', $R_1$, $R_2$, Ph and n are as defined above by oxidation to the sulfoxide. The oxidation can be carried out for example with sodium metaperiodate, as described by O. R. Johnson et al. in J. Am. Chem. Soc. 1965, 87, 1109. Generally aqueous alcoholic solutions and temperatures ranging from about −10 to about 50° C. are applied.

Preferably the oxidation is performed in aqueous methanol at temperature ranging from about 0 to about 25° C.

A compound of formula (VII) can be obtained from a compound of formula (VIII), wherein Y, R', Ph, $R_2$ and n are as defined above by N-acylation. The N-acylation can be carried out for example with acetic formic anhydride as described by S. Krishnamurthy in Tetrahedron Lett. 1982, 23, 3315. The reaction is typically performed in an inert organic solvent, preferably in THF solution, at temperatures ranging from about −25 to about 0° C.

A compound of formula (VIII) may be obtained from a compound of formula (IX), wherein Y, R', Ph, $R_2$ and n are as defined above by reduction.

For example the reduction can be accomplished by lithium aluminum hydride as described by N. G. Gaylord in "Reduction with Complex Metal Hydrides" (Interscience 1965). Preferably the reduction is carried out in a solvent mixture of ethyl ether and tetrahydrofuran a reflux temperatures.

A compound of formula (IX) can be obtained from a compound of formula (X), wherein Y, R', $R_2$ and n are as defined above, by conjugate addition of thiophenol. For example the reaction can be carried out as described by B. M. Trost et al. in J. Org. Chem. 1975, 40, 2013. Accordingly the conjugate addition of thiophenol is performed in THF solution in the presence of a catalytic amount of 4-dimethylaminopyridine at reflux temperatures.

A compound of formula (X) can be obtained from a compound of formula (V), wherein Y, R', $R_2$ and n are as defined above, by condensation with nitromethane. For example the modified method of D. E. Worrall (Organic Synthesis, Collect. Vol. I, p. 413) can be applied. For example the methanolic solution of the starting material is treated with aqueous sodium hydroxide at 0°-5° C. Then 40% HCl is added and the solution maintained at 60° C.

The new compounds of the present invention possess specific tyrosine kinase inhibiting activity. Hence they may be useful in the treatment of cancer and other pathological proliferative conditions.

Recent studies on the molecular basis of neoplastic transformation have identified a family of genes, designed oncogenes, whose aberrant expression causes tumorigenesis.

For example, the RNA tumor viruses possess such an oncogene sequence whose expression determines neoplastic conversion of infected cells. Several of their oncogene-encoded proteins, such as $pp60^{v-src}$, $p70^{gag-yes}$, $p130^{gag-fps}$ and $p70^{gag-fgr}$ display protein tyrosine kinase activity, that is they catalyse the transfer of the γ-phosphate from adenosine triphosphate (ATP) to tyrosine residues in protein substrate. In normal cells, several growth factor receptors, for example the receptors for PDGF, EGF, α-TGF and insulin, display tyrosine kinase activity. Binding of the growth factor (GF) activates the receptor tyrosine kinase to undergo autophosphorylation and to phosphorylate closely adjacent molecules on tyrosine.

Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyrosine kinase that are either overproduced and/or display altered substrate specificity may cause loss of growth control and/or neoplastic transformation. Therefore, a specific inhibitor of tyrosine kinases should be useful in investigating the mechanism of carcinogenesis, cell proliferation and differentiation and it may be effective in prevention and chemotherapy of cancer.

The tyrosine specific protein kinase activity of these compounds is shown, e.g., by the fact that they are active in the in vitro test described by B. Ferguson et al., in J. Biol. Chem. 1985, 260, 3652.

The enzyme used is the Abelson tyrosine kinase p $60^{v-abl}$. Its production and isolation is performed according to a modification of the method of B. Ferguson et al. (e.oc.cit.). As substrate α-casein or (Val$^5$)-angiotensin is used. The inhibitor is preincubated with the enzyme for 5 min at 25° C. The reaction conditions are: 100 mM MOPS buffer, 10 mM MhCl$_2$, 2 μm (6Ci/mmol), 1mg/ml γ-casein [an alternative substrate is (Val$^5$) angiotensin II] and 7.5 μg/ml of enzyme in a total volume of 30 μl and pH 7.0.

The reaction is incubated for 10 min at 25° C. Trichloroacetic acid precipitation of protein is followed by rapid filtration and quantification of phosphorylated substrate by a liquid scintillation counter. Alternatively the reaction mixture is subjected to sodium dodecyl sulfate —polyacrylamide electrophoresis and the phosphorylated substrate measured by autoradiography or $P^{32}$-counting of the excised spot.

In view of their high therapeutic index, the compounds of the invention can be used safely in medicine.

For example, the approximate acute toxicity (LD$_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar of film coated tablets, liquid solutions or suspensions; rectally, in the form of suppositories; parenterally, e.g. intramuscularly, or by intravenous injection of infusion; or topically.

The dosage depends on the age, weight, conditions of the patient and administration route; for example the dosage adopted for oral administration to adult humans may range from about 10 to about 150-200 mg pro dose, from 1 to 5 times daily. Of course, these dosage regimens may be adjusted to provide the optimal therapeutic response.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactures in known manner, for example, by means of mixing, granulating, tabletting sugar-coating or film-coating processes.

The liquid dispersion for oral administration may be e.g. syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusion may contain as carrier, for example, sterile water or, preferably, they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

Compositions for topical application e.g., creams, lotions or pastes, can be prepared by admixing the active ingredient with a conventional oleaginous or emulsifying excipient.

The following examples illustrate but do not limit the invention.

EXAMPLE 1

3-(2'-methoxynaphth-1'-yl) serine (IV, (A), R$_2$=H, R'=Me, N=1)

To a mixture of glycine (751 mg, 10 mmol) and 2-methoxy-1-naphthaldehyde (3724 mg, 20 mmol) in 50% ethanol (10 ml) is added a solution of sodium hydroxide (1400 mg, 35 mmol)in water (4 ml). The reaction mixture is stirred for 24 hrs, then acidified with 5M HCl (9 ml, 45 mmol) to pH 2 circa. The reaction mixture is extracted with chloroform. The organic layer contains about 1620 mg of the substrate (100% recovery) which can be recycled without further purification. The aqueous layer is brought to pH 5.5–6 that corresponds to the isoelectric point of the product.

The resulting precipitate is filtered after cooling, washed with water and dried under vacuum.

Thus 1700 mg (65% yield) of almost pure title compound are obtained; mp. 150°–160° C. dec.

From the mother liquor upon concentration other title compound can be obtained (130 mg, 5%)

The proceeding of the reaction and the threo/erythro isomer ratio is monitored by cellulose TLC using 50% butanol, 6% acetone, 6% conc. ammonia and 38% water for development.

C$_{14}$H$_{15}$O$_4$ requires: C 64.36 H 5.79 N 5.36.
found: C 64.25 H 5.65 N 5.25.
MS m/z: 261.
NMR δ(DMSO-d$_6$): 3.78 (d, J=10, 3 Hz, 1H, H-2) 3.85 (S, 3H, OCH$_3$), 5.61 (d, J=10, 3 Hz, 1H, H-3), 7.25–7.50 (m, 3H, H-3', H-7', H-6'), 7.80–7.95 (m, 2H, H-4', H-5'), 8.56 (d, J=8.4 Hz, 1H, H-8').

EXAMPLE 2

(E)-1-(N-formylaminovinyl)-2-methoxynaphthalene (I, (A), R=CH$_3$, R$_1$=R$_2$=H, n=1)

To a solution of 3-(2-methoxynaphth-1-yl) serine (2613 mg, 10 mmol) in 99% formic acid (2 ml) is added acetic anhydride (0.5 ml) and the resulting solution stirred for 2 hrs at room temperature. Then water is added and the mixture evaporated under vacuum.

The residue is chromatographed on a silica gel column using cyclohexane/ethyl acetate 1:1 as eluant to yield 1135 mg (50%) of pure title compound with m.p. 161°-2° C. C$_{14}$H$_{13}$NO$_2$ requires: C 73.99 H 5.76 N 6.16.
found: C 74.03 H 5.66 N 6.05.
MS m/z: 231.

NMR δ(DMSO-d$_6$): There is doubling of signals (approximately 4:1 mixture) due to the restricted rotation around the amid (N-C) bond. Only the signals of the major isomer are given here: 3.93 (S, 3H, OCH$_3$), 6.74 (d, J=14.8 H$_z$, 1H, Ar-CH=), 7.30 8.10 (m, 7H, H-3, H-4, H-5, H-6, H-7, H-8, =CH-N), 8.14 (S, IH, CHO), 10.30 (brd, J=13 Hz, 1H, NH) IR (KBr): 3250, 1660, 1640, 1615, 1585, 1530, 1240, 1090 cm$^{-1}$.

EXAMPLE 3

3-(2-methoxy-5,6,7,8-tetrahydronaphth-1-yl)-N-formylserine (II, (B), R'=CH$_3$, R$_1$=R$_2$=H, N=1)

To a solution of 3-(2-methoxy- 5,6,7,8-tetrahydronaphth-1-yl) serine (2653 mg, 10 mmol) in formic acid (4 ml) is added acetic anhydride (1 ml) and the resulting solution stirred for ½ h at room temperature.

Then water is added and the mixture evaporated under vacuum. The residue is crystallized from water thus giving 2490 mg 85% yield) of pure title compound.
C$_{15}$H$_{19}$NO$_5$ requires: C 61.42 H 6.53 N 4.78 .
found: C 61.33 H 6.45 N 4.65.
MS m/z: 293.

IR (K Br): 3100-3500 (OH, NH$_2$), 3000-2300 (COOH), 1720 (COOH), 1670 (CONMe$_2$), 1510 (c=c), 1500 (NH, C-N), 1220 and 1040 cm$^{-1}$ (C-O-C).

EXAMPLE 4

(E)-1-(N-formylaminovinyl)-2-methoxy-5, 6, 7, 8-tetrahydronaphthalene. [I, (B), R=CH$_3$, R$_1$=R$_2$=H, n=1]

A solution of 3-(2-methoxy-5, 6, 7, 8-tetrahydronaphth-1-yl)-N-formylserine (2930 mg, 10 mmol) and N,N-dimethylformamide dimethyl acetal (7100 mg, 60 mmol) in dry chloroform (50 ml) is heated at reflux temperature for 2 hrs. The reaction mixture is evaporated under vacuum, the residue dissolved in chloroform and filtered through a silica gel column. The eluateis evaporated under vacuum to give almost pure title compound in 85% yield (1970 mg).
C$_{14}$H$_{17}$NO$_2$ requires: C 72.70 H 7.41 N 6.06.
found: C 72.61 H 7.33 N 5.98.
MS m/z: 231.
IR (KBr): 3400, 1640, 1510, 1220, 1040 cm$^{-1}$.

EXAMPLE 5

(E)-1-(N-formylaminovinyl)-2-hydroxynaphthalene [I, (A), R=R$_1$=R$_2$=H, n=1]

To a stirred solution of (E)-N-[2-(2-methoxynaphth-1-yl) ethenyl] formamide (2273 mg, 10 mmol) in anhydrous dichloromethane (100 ml) is added at −79° C., under nitrogen, over a period of 10 min, a 1.0 M solution of boron tribromide in dichloromethane (30 ml, 30 mmol). The resulting mixture is stirred for another 1 hr at −78° C. and then allowed to warm to room temperature. After stirring for 1.5 hr at 20°-25° the mixture is cooled to −10° and then quenched by the dropwise addition of water (100 ml) over a 10-min period.

After addition of ethylacetate (100 ml) the organic layer is separated, washed with water, dried with Na$_2$SO$_4$ and evaporated under vacuum to dryness.

After venting with nitrogen the residue is dissolved in a minimal amount of CHCl$_3$/MeOH 10% and then the solution diluted with CHCl$_3$ to faint turbidity. The mixture is kept for several hours at 0°-5° C. and the precipitate is filtered and dried at room temperature under vacuum. Thus 1706 mg (80% yield) of pure title compound are obtained.

C$_{13}$H$_{11}$NO$_2$ requires: C 73.22 H 5.20 N 6.57.
found C 73.15 H 5.11 N 65.1.
MS m/z: 213.

IR (KBr) : 3350 (br), 1640, 1505, 1390, 1260, 1195, 950, 780 cm$^{-1}$.

NMR δ(acetone-d$_6$): 6.74 (d,J=14.8 Hz, IH, ArCH=) 7.30-8.10 (m, 7H,H-3, H-4, H-5, H-6, H-7, H-8, =CH-N) 7.70 (br S, IH, OH), 8.14 (S, IH, CHO), 10.30 (br d, J=13 Hz, IH, NH).

According to the above described procedure following compounds can be prepared:

2-(N-formylaminovinyl)-1-hydroxynaphthalene;
2-(N-formylaminovinyl)-3-hydroxynaphthalene;
2-(N-formylaminovinyl)-4-hydroxynaphthalene;
2-(N-formylaminovinyl)-1,4-dihydroxynaphthalene;
2-(N-formylaminovinyl)-1,3-dihydroxynaphthalene;
1-(N-formylaminovinyl)-3-hydroxynaphthalene;
1-(N-formylaminovinyl)-4-hydroxynaphthalene;
1-(N-formylaminovinyl)-3,4-dihydroxynaphthalene;
1-(N-formylaminovinyl)-2,4-dihydroxynaphthalene;
1-(N-formylaminovinyl)-2,3-dihydroxynaphthalene;
1-(N-formylaminovinyl)-2-hydroxy-tetralin;
1-(N-formylaminovinyl)-3-hydroxy-tetralin;
1-(N-formylaminovinyl)-4-hydroxy-tetralin;
1-(N-formylaminovinyl)-3,4-dihydroxy-tetralin;
1-(N-formylaminovinyl)-2,4-dihydroxy-tetralin;
1-(N-formylaminovinyl)-2,3-dihydroxy-tetralin;
2-(N-formylaminovinyl)-1-hydroxy-tetralin;
2-(N-formylaminovinyl)-3-hydroxy-tetralin;
2-(N-formylaminovinyl)-4-hydroxy-tetralin;
2-(N-formylaminovinyl)-1,3-dihydroxy-tetralin;
2-(N-formylaminovinyl)-1,4-dihydroxy-tetralin;
2-(N-formylaminovinyl)-3,4-dihydroxy-tetralin:
2-(N-formylaminovinyl)quinoline;
2-(N-formylaminovinyl)-3-hydroxyquinoline:
2-(N-formylaminovinyl)-4-hydroxyquinoline;
2-(N-formylaminovinyl)-5-hydroxyquinoline;
2-(N-formylaminovinyl)-6-hydroxyquinoline;
2-(N-formylaminovinyl)-7-hydroxyquinoline:
2-(N-formylaminovinyl)-8-hydroxyquinoline;
3-(N-formylaminovinyl)-quinoline;
3-(N-formylaminovinyl)-2-hydroxyquinoline;
3-(N-formylaminovinyl)-4-hydroxyquinoline:
3-(N-formylaminovinyl)-5-hydroxyquinoline;
3-(N-formylaminovinyl)-6-hydroxyquinoline;
3-(N-formylaminovinyl)-7-hydroxyquinoline;
3-(N-formylaminovinyl)-8-hydroxyquinoline;
4-(N-formylaminovinyl)-quinoline;
4-(N-formylaminovinyl)-2-hydroxyquinoline;
4-(N-formylaminovinyl)-3-hydroxyquinoline;
4-(N-formylaminovinyl)-5-hydroxyquinoline;
4-(N-formylaminovinyl)-6-hydroxyquinoline;

4-(N-formylaminovinyl)-7-hydroxyquinoline:
4-(N-formylaminovinyl)-8-hydroxyquinoline;
5-(N-formylaminovinyl)-quinoline;
5-(N-formylaminovinyl)-2-hydroxyquinoline;
5-(N-formylaminovinyl)-3-hydroxyquinoline;
5-(N-formylaminovinyl)-4-hydroxyquinoline;
5-(N-formylaminovinyl)-6-hydroxyquinoline;
5-(N-formylaminovinyl)-7-hydroxyquinoline;
5-(N-formylaminovinyl)-8-hydroxyquinoline;
8-(N-formylaminovinyl)-2-hydroxyquinoline;
8-(N-formylaminovinyl)-3-hydroxyquinoline;
8-(N-formylaminovinyl)-4-hydroxyquinoline;
8-(N-formylaminovinyl)-5-hydroxyquinoline;
8-(N-formylaminovinyl)-6-hydroxyquinoline;
8-(N-formylaminovinyl)-7-hydroxyquinoline;
1-(N-formylaminovinyl)-3-hydroxyisoquinoline;
1-(N-formylaminovinyl)-4-hydroxyisoquinoline;
1-(N-formylaminovinyl)-5-hydroxyisoquinoline;
1-(N-formylaminovinyl)-6-hydroxyisoquinoline;
1-(N-formylaminovinyl)-7-hydroxyisoquinoline;
1-(N-formylaminovinyl)-8-hydroxyisoquinoline;
3-(N-formylaminovinyl)-1-hydroxyisoquinoline;
3-(N-formylaminovinyl)-4-hydroxyisoquinoline;
3-(N-formylaminovinyl)-5-hydroxyisoquinoline;
3-(N-formylaminovinyl)-6-hydroxyisoquinoline;
3-(N-formylaminovinyl)-7-hydroxyisoquinoline;
3-(N-formylaminovinyl)-8-hydroxyisoquinoline;
2-(N-formylaminovinyl)-3-hydroxyiniole;
2-(N-formylaminovinyl)-4-hydroxyindole;
2-(N-formylaminovinyl)-5-hydroxyindole;
2-(N-formylaminovinyl)-6-hydroxyindole;
2-(N-formylaminovinyl)-7-hydroxyindole;
3-(N-formylaminovinyl)-2-hydroxyindole;
3-(N-formylaminovinyl)-4-hydroxyindole;
3-(N-formylaminovinyl)-5-hydroxyindole;
3-(N-formylaminovinyl)-6-hydroxyindole;
3-(N-formylaminovinyl)-7-hydroxyindole;
4-(N-formylaminovinyl)-2-hydroxyindole;
4-(N-formylaminovinyl)-3-hydroxyindole;
4-(N-formylaminovinyl)-5-hydroxyindole;
4-(N-formylaminovinyl)-6-hydroxyindole;
4-(N-formylaminovinyl)-7-hydroxyindole;
5-(N-formylaminovinyl)-2-hydroxyindole;
5-(N-formylaminovinyl)-3-hydroxyindole;
5-(N-formylaminovinyl)-4-hydroxyindole;
5-(N-formylaminovinyl)-6-hydroxyindole;
5-(N-formylaminovinyl)-7-hydroxyindole;
6-(N-formylaminovinyl)-2-hydroxyindole;
6-(N-formylaminovinyl)-3-hydroxyindole;
6-(N-formylaminovinyl)-4-hydroxyindole;
6-(N-formylaminovinyl)-5-hydroxyindole;
6-(N-formylaminovinyl)-7-hydroxyindole;
7-(N-formylaminovinyl)-2-hydroxyindole;
7-(N-formylaminovinyl)-3-hydroxyindole;
7-(N-formylaminovinyl)-4-hydroxyindole;
7-(N-formylaminovinyl)-5-hydroxyindole; and
7-(N-formylaminovinyl)-6-hydroxyindole.

EXAMPLE 6

(E)-1-(N-formylaminovinyl)-2-acetoxynaphthalene (I, (A), R=CH$_3$CO, R$_1$=R$_2$=H, n=1)

To a cooled solution of (E)-N-[2-(2-hydroxynaphth-1-yl) ethenyl] formamide (2133 mg, 10 mmol) in dry pyridine (5 ml) is added acetic anhydride (2042 mg, 20 mmol) and the mixture maintained at 0°-5° overnight. Thereupon the mixture is concentrated under vacuum, the residue dissolved in dichloromethane, the organic layer washed with water and then evaporated under reduced pressure. The crude product is crystallized from chloroform/methanol to yield pure title compound in 90% yield (2300 mg).

$C_{15}H_{13}NO_3$ requires: C 70.58 H 5.13 N 5.49.
found: C 70.45 H 5.01 N 5.40.
MS m/z: 255.
IR (KBr): 3400, 1750, 1640, 1505, 1395, 1250, 1200 cm$^{-1}$.

EXAMPLE 7

1-(2-methoxynaphth-1-yl)-2-nitroethene (X, (A), R=CH$_3$, R$_2$=H, n=1)

A mixture of 2-methoxy-1-naphthaldehyde (1862 mg, 10 mmol) and nitromethane (610 mg, 10 mmol) in methanol (200 ml) is stirred at room temperature until the solids dissolved. The solution is cooled to about 0° C. and a 30% NaOH solution (2 ml, 20 mmol) is added dropwise over 30 min. The resulting solution is added slowly at 60° C. to a 35% HCl solution (200 ml). The amorphous solid that formed is filtered and washed with water. The crude product is recrystallized from ethanol to give pure title compound in 80% yield (1835 mg).

$C_{13}H_{11}NO_3$ requires: C 68.11 H 4.89 H 6.11.
found: C 68.05 H 4.79 N 5.99.
MS m/z: 229.
IR (KBr): 3120, 1620, 1500, 1350 cm$^{-1}$.

EXAMPLE 8

1-(2-methoxynaphth-1-yl)-1-(phenylthio)-2-nitroethane (IX, (A), R=CH$_3$, R$_2$=H, n=1)

A mixture of 1-(2-methoxynaphth-1-yl)-2-nitroethene (2293 mg. 10 mmol) and thiophenol (2204 mg. 20 mmol) and a catalytic amount of 4-(dimethylamino)-pyridine in dry THF (120 ml) is heated at reflux for 5 h.

The solvent is removed under reduced pressure and the residue taken up in ether. The ether extract is washed with dilute NaOH solution and then with dilute HCl solution. The ethereal layer is dried over Na$_2$SO$_4$ and then evaporated in vacuo to give almost pure title compound in 95% yield (3224 mg).

$C_{19}H_{17}NO_3S$ requires: C 67.24 H 5.05 N 4.13 S 9.45.
found: C 67.12 H 4.95 N 4.05 S 9.36.
MS m/z: 339.
IR (KBr): 1550, 1510, 1370, 1210, 1040 cm$^{-1}$.

EXAMPLE 9

1-(2-methoxynaphth-1-yl)-1-(phenylthio)-2-aminoethane (VIII, (A), R=CH$_3$, R$_2$=H, n=1)

To a vigorously stirred suspension of lithium aluminum hydride (76 mg. 20 mmol) in anhydrous ether - THF 2:1 solvent mixture (80 ml) a solution of 1-(2-methoxynaphth-1-yl)-1-(phenylthio)-2-nitroethane (3394 mg, 10 mmol) in ether- THF 2:1 (40 ml) is added dropwise. The reaction mixture is heated at reflux for 24 h and then cooled to 0° C. Ether is added and the excess of LiAlH$_4$ is destroyed by the cautious successive addition of water (2 ml) and 2N NaOH solution (4 ml). The aluminum salts are filtered off and the organic layer evaporated in vacuo. The residue is dissolved in ether and the ethereal solution extracted with 2N HCl solution. The aqueous acidic layer is brought to pH 9 by addition of 2N NaOH and extracted with ether. The ethereal layer is dried with Na$_2$SO$_4$ and then evaporated to dryness in vacuo to give almost pure title compound in 70% yield (2165 mg).

$C_{19}H_{19}NOS$ required: C 73.75 H 6.19 N 4.53 S 10.36.
found: C 73.61 H 6.15 N 4.45 S 10.25.
MS m/z: 309.
IR (KBr): 3400, 1600, 1220, 1040 cm$^{-1}$.

EXAMPLE 10

1-(1-phenylthio-2-formylaminoethyl)-2-methoxynaphthalene (VII, (A), R=CH$_3$, R$_1$=R$_2$=H, n=1)

Acetic formic anhydride is generated by dropwise addition of 98% formic acid (1472 mg, 32 mmol) to 2655 mg (26 mmol) of acetic anhydride maintained at 0° C. followed by gentle heating at 50°-60° C. for 2 h. The mixture is cooled to −15° C. and 20 ml of THF are added. To the resulting solution is added dropwise at −15° C. a solution of 1-(2-methoxynaphth-1-yl)-1-(phenylthio)-2-aminoethane (3094 mg, 10 mmol) in THF (50 ml). The reaction mixture is allowed to warm to room temperature and the volatiles are removed in vacuo. The residue is taken up in ether. The ether solution is washed with water and NaHCO$_3$ solution, dried over anhydrous K$_2$CO$_3$ and then evaporated in vacuo. The oily residue is triturated with ethyl acetate-hexane mixture to give crystalline title compound in 85% yield (2870 mg).

$C_{20}H_{19}NO_2S$ requires: C 71.19 H 5.68 N 4.15 S 9.50.
found: C 71.12 H 5.55 N 4.03 S 9.35.
MS m/z: 337.
(KBr): 3240, 1650, 1500, 1220, 1040 cm$^{-1}$.

EXAMPLE 11

1-(1-phenylsulfinyl-2-formylaminoethyl)-2-methoxy-naphthalene (III, (A), R=CH$_3$, R$_1$=R$_2$=H, n=1)

A concentrated solution of sodium metaperiodate (2139 mg, 10 mmol) in water is added dropwise at 0° C. under cooling to a solution of 1-(1-phenylthio-2-formylaminoethyl)-2-methoxy-naphthalene (3374 mg, 10 mmol) in methanol (100 ml). The reaction is then stirred at room temperature for 24 h. The solids are filtered off and washed several times with ethyl acetate (1000 ml). The filtrate and washings are combined and then evaporated under vacuum to yield crude title compound in about 100% yield (3534 mg) which is used in the next step without further purification.

EXAMPLE 12

(E)-1-(N-formylaminovinyl)-2-methoxynaphthalene [I, (A), R=CH$_3$, R$_1$=R$_2$=H, n=1]

To a solution of 1-(1-phenylsulfinyl-2-formylaminoethyl)-2-methoxynaphthalene (3534 mg, 10 mmol) in toluene (60 ml) is added sodium carbonate (1060 mg, 10 mmol) and the mixture heated at reflux for 6 h. Then the mixture is filtered after cooling and the filtrate concentrated in vacuo. The residue is subjected to column chromatography over silica gel using as eluant cyclohexane/ethyl acetate (1:1) to give pure title compound with m.p. 160°-2° C., in 90% yield (1850 mg).

$C_{14}H_{13}NO_2$ requires: C 73.99 H 5.76 N 6.16.
found: C 74.03 H 5.66 N 6.05.
MS m/z: 231.
NMR δ(DMSO-d$_6$): There is doubling of signals (approximately 4:1 mixture) due to the restricted rotation around the amid (N-C) bond. Only the signals of the major isomer are given here.
3.93 (S, 3H, OCH$_3$), 6.74 (d, J=14.9 Hz, 1H, Ar-CH=), 7.30–8.10 (m, 7H, H-3, H-4, H-5, H-6, H-7, H-8, =CH-N), 8.14 (S, 1H, CHO), 10.30 (brd, J=13 Hz, 1H, NH).
IR (KBr): 3250, 1660, 1640, 1615, 1585, 1530, 1240, 1090 cm$^{-1}$.

The compound obtained in this manner can be demethylated as described in example 5 to yield (E)-1-(N-formylaminovinyl)-2-hydroxy-naphthalene.

According to the above described procedure, and starting from the appropriate precursor of formula (III) and after demethylation as described in example 5, all the compounds occurring in Example 5 can be prepared.

EXAMPLE 13

Tablets each weighing 0.150 g and containing 25 mg of the active substance, can be manufactured as follows: composition (for 10000 tablets):

| | |
|---|---|
| (E)-1-(N-formylaminovinyl)-2-hydroxynaphthalene | 250 g |
| Lactose | 800 g |
| Corn starch | 415 g |
| Talc powder | 30 g |
| Magnesium stearate | 5 g |

The (E)-1-(N-formylaminovinyl)-2-hydroxynaphthalene, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 14

Capsules, each dosed at 0.200 g and containing 20 mg of the active substance can be prepared. Composition for 500 capsules:

| | |
|---|---|
| (E)-1-(N-formylaminovinyl)-2-hydroxynaphthalene | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A compound of formula (I)

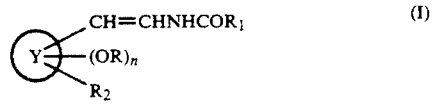

wherein
Y is a bicyclic ring system chosen from (A) and (B).

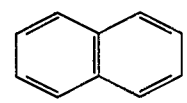

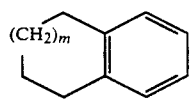 (B)

in which m is zero, 1 or 2;
R is hydrogen, a $C_1$–$C_6$ alkyl or $C_1$–$C_6$ alkanoyl group;
$R_1$ is hydrogen or $C_1$–$C_6$ alkyl;
$R_2$ is hydrogen, halogen, cyano or $C_1$–$C_6$ alkyl; and
n is an integer of 1 to 3; and wherein each of the substituents —CH=CHNHCOR$_1$, OR and $R_2$ may be independently on either of the aryl and heteroaryl moieties of the bicyclic ring system (A) whereas only the benzene ring may be substituted in the bicyclic ring system (B).

2. A compound of formula (I), according to claim 1, wherein
Y is a bicyclic ring system as defined in claim 1;
R is hydrogen or $C_1$–$C_4$ alkyl;
$R_1$ is hydrogen or $C_1$–$C_4$ alkyl;
$R_2$ is hydrogen; and
n is as defined in claim 1.

3. A compound of formula (I), according to claim 1, wherein
Y is a bicyclic ring system as defined in claim 1;
each of R, $R_1$ and $R_2$ is hydrogen; and
n is 1 or 2.

4. A compound as defined in claim 1, selected from the group consisting of the following, which, when appropriate, may be either Z- or E-diastereomers or Z, E-mixtures of said diastereomers:

2-(N-formylaminovinyl)-1-hydroxynaphthalene;
2-(N-formylaminovinyl)-3-hydroxynaphthalene;
2-(N-formylaminovinyl)-4-hydroxynaphthalene;
2-(N-formylaminovinyl)-1,4-dihydroxynaphthalene;
2-(N-formylaminovinyl)-1,3-dihydroxynaphthalene;
1-(N-formylaminovinyl)-2-hydroxynaphthalene;
1-(N-formylaminovinyl)-3-hydroxynaphthalene;
1-(N-formylaminovinyl)-3,4-dihydroxynaphthalene;
1-(N-formylaminovinyl)-2,4-dihydroxynaphthalene;
1-(N-formylaminovinyl)-2,3-dihydroxynaphthalene;
1-(N-formylaminovinyl)-2-hydroxy-tetrahydronaphthalene;
1-(N-formylaminovinyl)-3-hydroxy-tetrahydronaphthalene;
1-(N-formylaminovinyl)-4-hydroxy-tetrahydronaphthalene;
1-(N-formylaminovinyl)-3,4-dihydroxy-tetrahydronaphthalene;
1-(N-formylaminovinyl)-2,4-dihydroxy-tetrahydronaphthalene;
1-(N-formylaminovinyl)-2,3-dihydroxy-tetrahydronaphthalene;
2-(N-formylaminovinyl)-1-hydroxy-tetrahydronaphthalene;
2-(N-formylaminovinyl)-3-hydroxy-tetrahydronaphthalene;
2-(N-formylaminovinyl)-4-hydroxy-tetrahydronaphthalene;
2-(N-formylaminovinyl)-1,3-dihydroxy-tetrahydronaphthalene;
2-(N-formylaminovinyl)-1,4-dihydroxy-tetrahydronaphthalene;
2-(N-formylaminovinyl)-3,4-dihydroxy-tetrahydronaphthalene;
1-(N-formylaminovinyl)2-methoxynaphthalene;
1-(N-formylaminovinyl)-2-methoxy-5,6,7,8-tetrahydronaphthalene; and
1-(N-formylaminovinyl)-2-acetoxynaphthalene.

5. A pharmaceutical composition comprising a suitable carrier and/or diluent and, as an active principle, a compound of formula (I) according to claim 1.

6. A method of inhibiting tyrosine kinase which comprises applying an effective amount of a compound of formula (I) according to claim 1.

* * * * *

UNITED STATES PATENT AND TRADEMARK OFFICE
CERTIFICATE OF CORRECTION

PATENT NO. : 5,122,537
DATED : June 16, 1992
INVENTOR(S) : Franco BUZZETTI

It is certified that error appears in the above-identified patent and that said Letters Patent is hereby corrected as shown below:

Please correct claim 4, column 18 line 39, by adding the third compound as follows:

--1-(N-formylaminovinyl)-4-hydroxynaphthalene--.

Signed and Sealed this

Nineteenth Day of October, 1993

Attest:

BRUCE LEHMAN

Attesting Officer

Commissioner of Patents and Trademarks